(12) United States Patent
Gerberding

(10) Patent No.: US 7,537,607 B2
(45) Date of Patent: May 26, 2009

(54) STENT GEOMETRY FOR IMPROVED FLEXIBILITY

(75) Inventor: Brent C. Gerberding, Alameda, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1315 days.

(21) Appl. No.: 10/026,413

(22) Filed: Dec. 21, 2001

(65) Prior Publication Data

US 2003/0120334 A1    Jun. 26, 2003

(51) Int. Cl.
*A61F 2/06* (2006.01)
(52) U.S. Cl. ..................................... 623/1.15
(58) Field of Classification Search ............... 623/1.15, 623/1.16, 1.18, 1.19, 1.2, 1.4; 606/191, 194
See application file for complete search history.

(56) References Cited

U.S. PATENT DOCUMENTS

| | | | |
|---|---|---|---|
| 5,091,205 A | 2/1992 | Fan | 427/2 |
| 5,725,548 A * | 3/1998 | Jayaraman | 623/1.15 |
| 5,755,770 A | 5/1998 | Ravenscroft | 623/1 |
| 5,824,046 A | 10/1998 | Smith et al. | 623/1 |
| 5,935,162 A * | 8/1999 | Dang | 623/1.15 |
| 5,957,930 A | 9/1999 | Vrba | 606/108 |
| 6,013,091 A | 1/2000 | Ley et al. | |
| 6,117,165 A | 9/2000 | Becker | |
| 6,120,522 A | 9/2000 | Vrba et al. | 606/190 |
| 6,123,712 A | 9/2000 | DiCaprio et al. | 606/108 |
| 6,231,599 B1 | 5/2001 | Ley | |
| 6,280,457 B1 | 8/2001 | Wallace et al. | 606/200 |
| 6,395,020 B1 | 5/2002 | Ley et al. | |
| 6,416,538 B1 | 7/2002 | Ley et al. | |

(Continued)

FOREIGN PATENT DOCUMENTS

EP    0 806 190 A1    11/1997

(Continued)

OTHER PUBLICATIONS

U.S. Appl. No. 60/238,178, filed Oct. 5, 2000, DiCaprio et al.

(Continued)

*Primary Examiner*—Eduardo C Robert
*Assistant Examiner*—David Comstock
(74) *Attorney, Agent, or Firm*—Vidas, Arrett & Steinkraus, P.A.

(57) ABSTRACT

A stent comprises one or more circumferential serpentine bands and having alternating peak portions and trough portions. The peak portions include shorter peak portions and longer peak portions. The longer peak portions are of a longitudinal extent greater than the shorter peak portions. The longer peak portions include first bent peak portions which extend in a first direction non-parallel to the longitudinal axis of the stent and second bent peak portions which extend in a second direction non-parallel to the longitudinal axis of the stent. Each first bent peak portion is circumferentially adjacent to one second bent peak portion which points toward the first bent peak portion and to one second bent peak portion which points away from the first bent peak portion. Adjacent first and second bent peak portions which point toward one another are separated one from the other by at least one shorter peak portion.

21 Claims, 4 Drawing Sheets

U.S. PATENT DOCUMENTS

| | | |
|---|---|---|
| 6,506,211 B1 * | 1/2003 | Skubitz et al. ............. 623/1.15 |
| 6,835,203 B1 * | 12/2004 | Vardi et al. ................ 623/1.34 |
| 2002/0111669 A1 | 8/2002 | Pazlenza et al. |
| 2002/0151962 A1 | 10/2002 | Ley et al. |
| 2004/0093058 A1 | 5/2004 | Cottone et al. |
| 2004/0093073 A1 | 5/2004 | Lowe et al. |
| 2005/0090894 A1 | 4/2005 | Pazienza et al. |
| 2005/0107865 A1 | 5/2005 | Clifford et al. |
| 2006/0015173 A1 | 1/2006 | Clifford et al. |

FOREIGN PATENT DOCUMENTS

| | | | | |
|---|---|---|---|---|
| EP | 1 132 060 | 9/2001 | | |
| WO | 99/01888 | 4/1999 | | |
| WO | WO 99/36002 | * | 7/1999 | ................ 623/1.34 |
| WO | 99/44543 | 9/1999 | | |
| WO | 00/42945 | 7/2000 | | |
| WO | 00/42946 | 7/2000 | | |
| WO | 02/054986 | 7/2002 | | |

OTHER PUBLICATIONS

U.S. Appl. No. 10/160,494, filed May 31, 2002, Ley et al.

U.S. Appl. No. 10/131,772, filed Apr. 23, 2002, Ley.

* cited by examiner

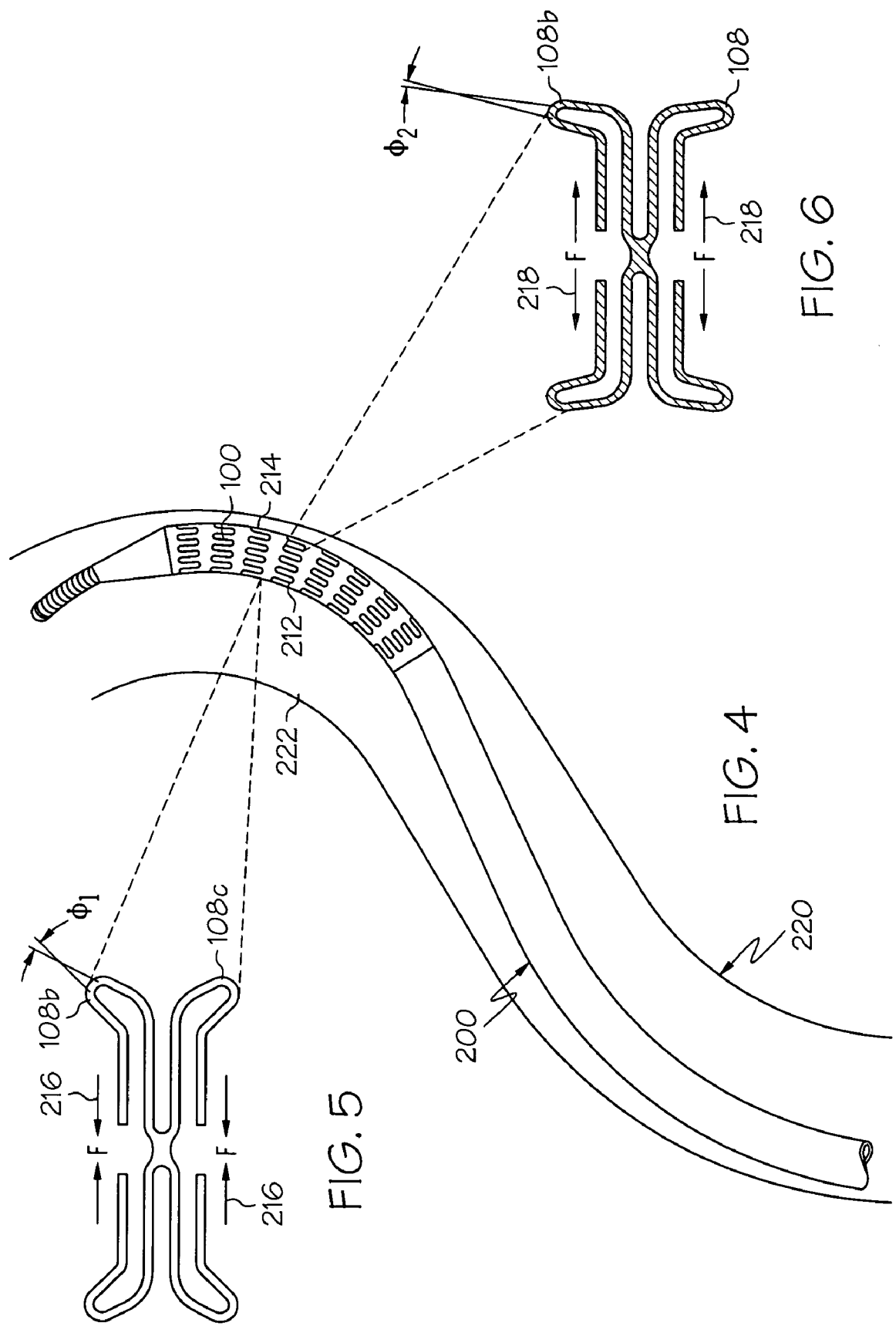

STENT GEOMETRY FOR IMPROVED FLEXIBILITY

BACKGROUND OF THE INVENTION

The use of stents in bodily lumen is well known. A stent is typically delivered in an unexpanded state to a desired location in a bodily lumen and then expanded. The stent may be expanded via the use of mechanical device such as a balloon or the stent may be self-expanding.

Because a stent often must be delivered through tortuous anatomy, it is desirable for the stent to be flexible. Increased flexibility in a stent, however, typically comes at the expense of scaffolding strength. Moreover, design features which may result in increased flexibility may also result in protruding edges which may damage vessels walls or catheter balloons during delivery of the stent through tortuous vasculature.

Extra flexibility is particularly desirable in self-expanding stents which, during delivery, are typically restrained via a restraining sheath on a catheter.

There remains a need for a stent which has a high degree of flexibility in the unexpanded state and has adequate scaffolding strength.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent comprising at least one serpentine band extending about the circumference of the stent and having alternating peak portions and trough portions. The peak portions include shorter peak portions and longer peak portions. The longer peak portions are of a longitudinal extent greater than the shorter peak portions. The longer peak portions include first bent peak portions which extend in a first direction non-parallel to the longitudinal axis of the stent and second bent peak portions which extend in a second direction non-parallel to the longitudinal axis of the stent. Each first bent peak portion is circumferentially adjacent to one second bent peak portion which points toward the first bent peak portion and to one second bent peak portion which points away from the first bent peak portion. Adjacent first and second bent peak portions which point toward one another are separated one from the other by at least one shorter peak portion.

Desirably, the trough portions of the serpentine band include shorter trough portions and longer trough portions. The longer trough portions are of a longitudinal extent greater than the shorter trough portions. The longer trough portions include first bent trough portions which extend in a first direction nonparallel to the longitudinal axis of the stent and second bent trough portions which extend in a second direction non-parallel to the longitudinal axis of the stent. Each first bent trough portion is circumferentially adjacent to one second bent trough portion which points toward the first bent trough portion and to one second bent trough portion which points away from the first bent trough portion. Adjacent first and second bent trough portions which point toward one another are separated one from the other by at least one shorter trough portion.

Typically, the inventive stents comprise a plurality of the serpentine bands. Serpentine bands which are longitudinally adjacent one another are connected one to the other by at least one longitudinal connector and desirably a plurality of longitudinal connectors extending from shorter peak portions of one serpentine band to shorter trough portions on a serpentine band which is longitudinally adjacent thereto.

In some embodiments of the invention, adjacent first and second bent trough portions which point away from one another are separated one from the other by one or more shorter trough portions and adjacent first and second bent peak portions which point away from one another are separated by one or more shorter peak portions.

In other embodiments of the invention, adjacent first and second bent trough portions which point away from one another are not separated by any shorter trough portions and adjacent first and second bent peak portions which point away from one another are not separated by any shorter peak portions.

Typically, adjacent first and second bent trough portions which point away from one another are not separated by any shorter trough portions, adjacent first and second bent peak portions which point away from one another are not separated by any shorter peak portions, adjacent first and second bent trough portions which point toward one another are separated one from the other by at least two shorter trough portions and adjacent first and second bent peak portions which point toward one another are separated one from the other by at least two shorter peak portions.

The invention is also directed to a stent comprising at least one serpentine band with a plurality of alternating peak portions and trough portions. The peak portions include at least two bent peak portions which bend toward one another. Each of the bent peak portions wraps at least partially about an adjacent peak portion. Desirably, the trough portions include at least two bent trough portions which bend toward one another. Each of the bent trough portions wraps at least partially about an adjacent trough portion.

Typically, the inventive stents will comprise a plurality of the serpentine bands. Where multiple serpentine bands are present, adjacent serpentine bands may be connected one to the other via at least one, and desirably, a plurality of connectors extending from a peak portion of one serpentine band to a trough portion of an adjacent serpentine band. The connectors may extend from any portion of one serpentine band to any other portion of an adjacent serpentine band. Desirably, adjacent serpentine bands are connected one to the other via a plurality of connectors extending from peak portions of one serpentine band to trough portions of an adjacent serpentine band. More desirably, each connector has a first end and a second end and the first and second end circumferentially aligned one with the other. Even more desirably, the connectors are parallel to the longitudinal axis of the stent.

Desirably, the inventive stents are made of one or more shape memory materials.

Also desirably, the inventive stents are constructed and arranged to be self-expanding.

The invention is also directed to the combination of an inventive stent disclosed herein disposed on a catheter. Desirably, the stent is self-expanding and is restrained by a sheath.

Additional details and/or embodiments of the invention are discussed below.

BRIEF DESCRIPTION OF THE DRAWINGS

FIG. 4 shows a side view of a portion of a catheter with a stent mounted thereon taken in cross-section as it may appear as it is advanced through a vessel.

FIG. 5 shows an enlarged side view of a portion of the stent shown in FIG. 4, on application of a substantially inward acting force.

FIG. 6 shows an enlarged side view of a portion of the stent shown in FIG. 4, on application of a substantially outward acting force.

DETAILED DESCRIPTION OF THE INVENTION

Figure 1:
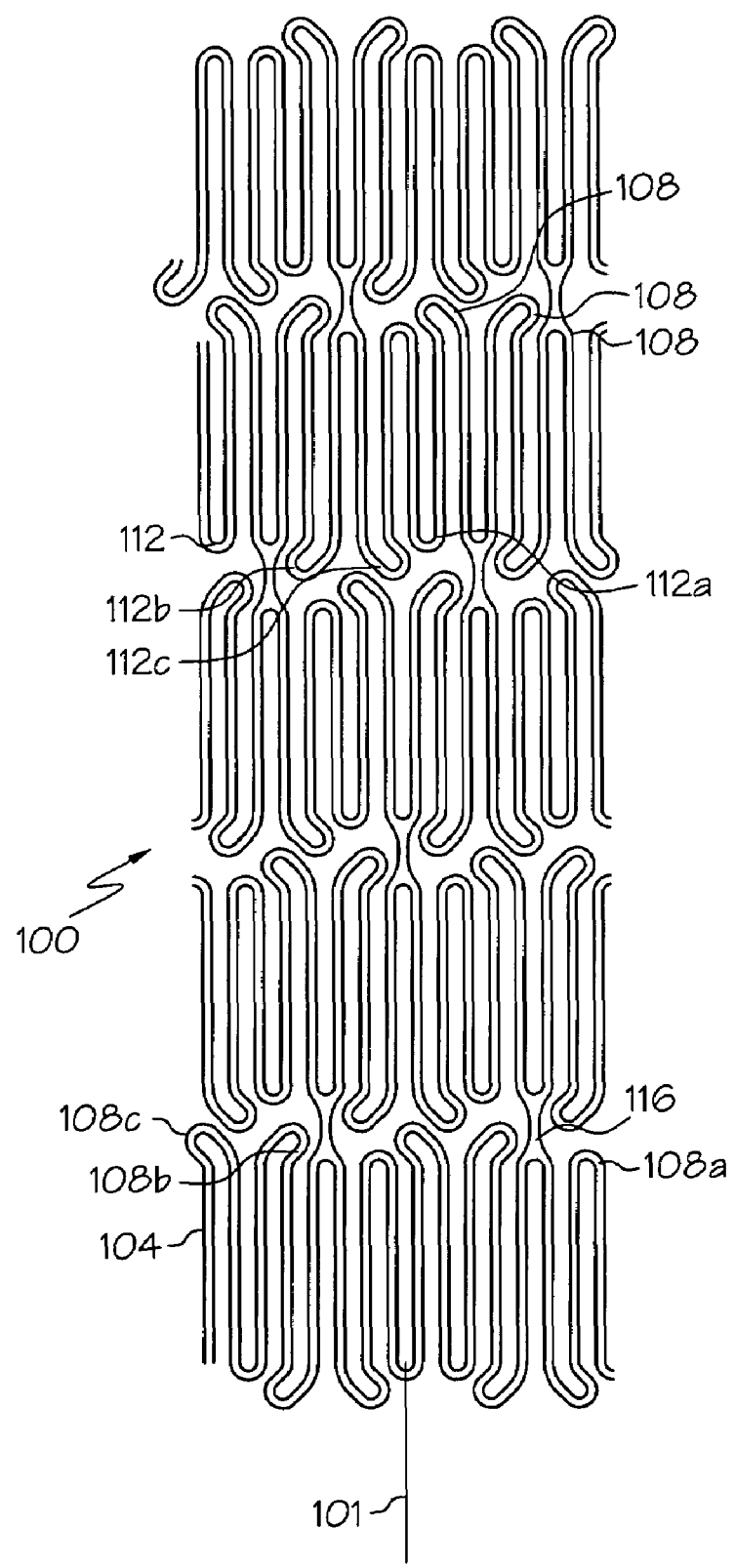
FIG. 1 is a flat layout view of an inventive stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a stent such as that shown by way of example at 100 in FIG. 1, comprising at least one serpentine band 104 extending about the circumference of the stent and having alternating peak portions 108 and trough portions 112. The peak portions include shorter peak portions 108a and longer peak portions 108b,c. The longer peak portions are of a longitudinal extent greater than the shorter peak portions. The longer peak portions include first bent peak portions 108b which extend in a first direction non-parallel to the longitudinal axis 101 of the stent and second bent peak portions 108c which extend in a second direction non-parallel to the longitudinal axis of the stent. Each first bent peak portion 108b is circumferentially adjacent to one second bent peak portion 108c which points toward a first bent peak portion and to one second bent peak portion which points away from the first bent peak portion. Adjacent first and second bent peak portions 108b and 108c which point toward one another are separated one from the other by at least one shorter peak portion 108a.

Desirably, the trough portions 112 of the serpentine band include shorter trough portions 112a and longer trough portions 112b, 112c. The longer trough portions are of a longitudinal extent greater than the shorter trough portions. The longer trough portions include first bent trough portions 112b which extend in a first direction non-parallel to the longitudinal axis of the stent and second bent trough portions 112c which extend in a second direction non-parallel to the longitudinal axis of the stent. Each first bent trough portion is circumferentially adjacent to one second bent trough portion which points toward the first bent trough portion and to one second bent trough portion which points away from the first bent trough portion. Adjacent first and second bent trough portions which point toward one another are separated one from the other by at least one shorter trough portion.

The inventive stents disclosed herein may comprise a single such serpentine band 104 or a plurality of such serpentine bands, as shown in FIG. 1. In the latter case, where the stent includes such serpentine bands which are longitudinally adjacent one another, the adjacent serpentine bands are connected one to the other. Desirably, adjacent serpentine bands are connected by one or more connectors. The connectors may extend in a longitudinal direction as shown in FIG. 1. Connectors 116 of FIG. 1 have straight sides and extend longitudinally. The connectors may also include one or more curved portions as long as the first and second ends of the connectors are circumferentially aligned with one another. Curved or straight connectors whose first and second ends are longitudinally and circumferentially offset from one another may be used in conjunction with the serpentine segments disclosed herein in other embodiments of the invention. In the embodiment of FIG. 1, the connectors are shorter in length than the longitudinal extent of the serpentine bands. The invention contemplates closely spaced serpentine bands, as shown in FIG. 1, serpentine bands which abut one another as well as serpentine bands which are spaced further apart than the spacing shown in FIG. 1. To that end, the connectors may be as long as the serpentine bands or longer.

Figure 7:
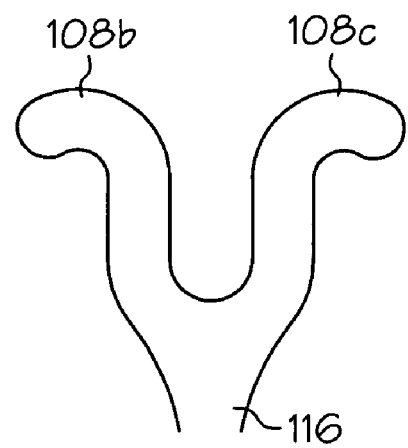
FIG. 7 is a flat layout view of a portion of a stent.

In an alternative embodiment of the invention shown in FIG. 7, each connector 116 is associated with at least two peak portions 108b and 108c.

As shown in FIG. 1, connectors 116 desirably extend from shorter peak portions of one serpentine band to shorter trough portions on a serpentine band which is longitudinally adjacent thereto.

In some embodiments of the invention, such as for example, the embodiment of FIG. 1, adjacent first and second bent trough portions which point away from one another are separated one from the other by one or more shorter trough portions and adjacent first and second bent peak portions which point away from one another are separated by one or more shorter peak portions.

In other embodiments of the invention, adjacent first and second bent trough portions which point away from one another are not separated by any shorter trough portions and adjacent first and second bent peak portions which point away from one another are not separated by any shorter peak portions.

Typically, as shown in FIG. 1, adjacent first and second bent trough portions which point away from one another are not separated by any shorter trough portions, adjacent first and second bent peak portions which point away from one another are not separated by any shorter peak portions, adjacent first and second bent trough portions which point toward one another are separated one from the other by at least two shorter trough portions and adjacent first and second bent peak portions which point toward one another are separated one from the other by at least two shorter peak portions.

The invention is also directed to a stent, such as that shown by way of example in FIG. 1, comprising at least one serpentine band 104 with a plurality of alternating peak portions 108 and trough portions 112. The peak portions include at least two bent peak portions 108b and 108c which bend toward one another. Each of the bent peak portions wraps at least partially about an adjacent peak portion 108a. Desirably, the trough portions 112 include at least two bent trough portions 112b and 112c which bend toward one another. Each of the bent trough portions wraps at least partially about an adjacent trough portion 112a.

Typically, the inventive stents will comprise a plurality of the serpentine bands 104. Where multiple serpentine bands are present, adjacent serpentine bands may be connected one to the other via at least one, and desirably, a plurality of connectors extending from a peak portion of one serpentine band to a trough portion of an adjacent serpentine band. The connectors may extend from any portion of one serpentine band to any other portion of an adjacent serpentine band. Desirably, adjacent serpentine bands are connected one to the other via a plurality of connectors extending from peak portions of one serpentine band to trough portions of an adjacent serpentine band. More desirably, each connector has a first end and a second end and the first and second end circumferentially aligned one with the other. Even more desirably, as shown in FIG. 1, the connectors are parallel to the longitudinal axis of the stent.

Figure 2:
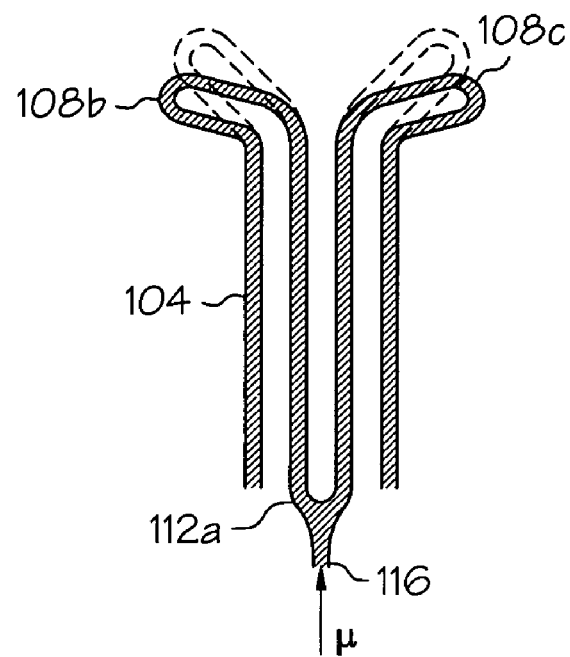
FIG. 2 shows the flexing of a portion of the stent on application of a force thereto.

Because of the presence of circumferentially adjacent longer first and second peak portions 108b and 108c which point toward one another and which are separated one from the other by at least one shorter peak portion 108a, a longitudinal force transmitted through a connector 116 will be deflected off to the sides, as shown in FIG. 2 thereby allowing cells to open and close. Also, because of the presence of circumferentially adjacent longer first and second trough portions 112b and 112c which point toward one another and which are separated one from the other by at least one shorter trough portion 112a, a longitudinal force transmitted through a connector 116 will be deflected off to the sides thereby allowing cells to open and close.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the circumferential serpentine bands and/or connectors may increase or decrease along portions of the stent or along the entire length of the stent. The longitudinal extent and number of peaks and troughs of several successive serpentine bands may remain constant while the width and/or thickness of the successive serpentine bands decreases. Similarly, the longitudinal extent and number of peaks and troughs of several successive serpentine bands may remain constant while the width and/or thickness of the successive serpentine bands decreases.

The inventive stents may also be modified, by choice of material or geometry so that one or both ends are more rigid or more flexible than the remainder of the stent.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design. The stent may also be manufactured by welding individual sections, for example, circumferential bands, together. Any other suitable stent manufacturing process may also be used.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals including nickel-titanium alloys generically known as "nitinol", platinum/tungsten alloys and titanium alloys.

The invention also contemplates the use of more than one material in the inventive stents. For example, the serpentine bands may be made of different materials. Optionally, the connectors may be made of a different material than the serpentine bands.

The inventive stents may be provided in mechanically expandable form, in self-expanding form or as a hybrid of the two. Mechanically expandable stents, in accordance with the invention, may be expanded using any suitable mechanical device including a balloon. Desirably, the inventive stents are made in self-expanding form.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14,BMP-15, and BMP-16. Desirable BMP's are any of BMP-2,BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

Other polymer materials that may be utilized with the present invention include matrix compounds that induce inflammation of the vessel. Some examples of such matrix compounds include but are not limited to: lactide, glycolide, and caprolactone polymers and their copolymers; hydroxybutyrate and polyhydroxyvalerate and their block and random copolymers; a polyether ester; anhydrides, polymers and copolymers of sebacic acid, hexadecandioic acid; orthoesters; polydioxinone; polyglycolic acid and polylactic acid, their block and random copolymers. Other compounds my be included such as are described in U.S. Pat. No. 6,280,457, the contents of which are incorporated in their entirety herein by reference.

The inventive stents may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends and copolymers.

The inventive stents may find use in coronary arteries, renal arteries, peripheral arteries including iliac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

Figure 3:
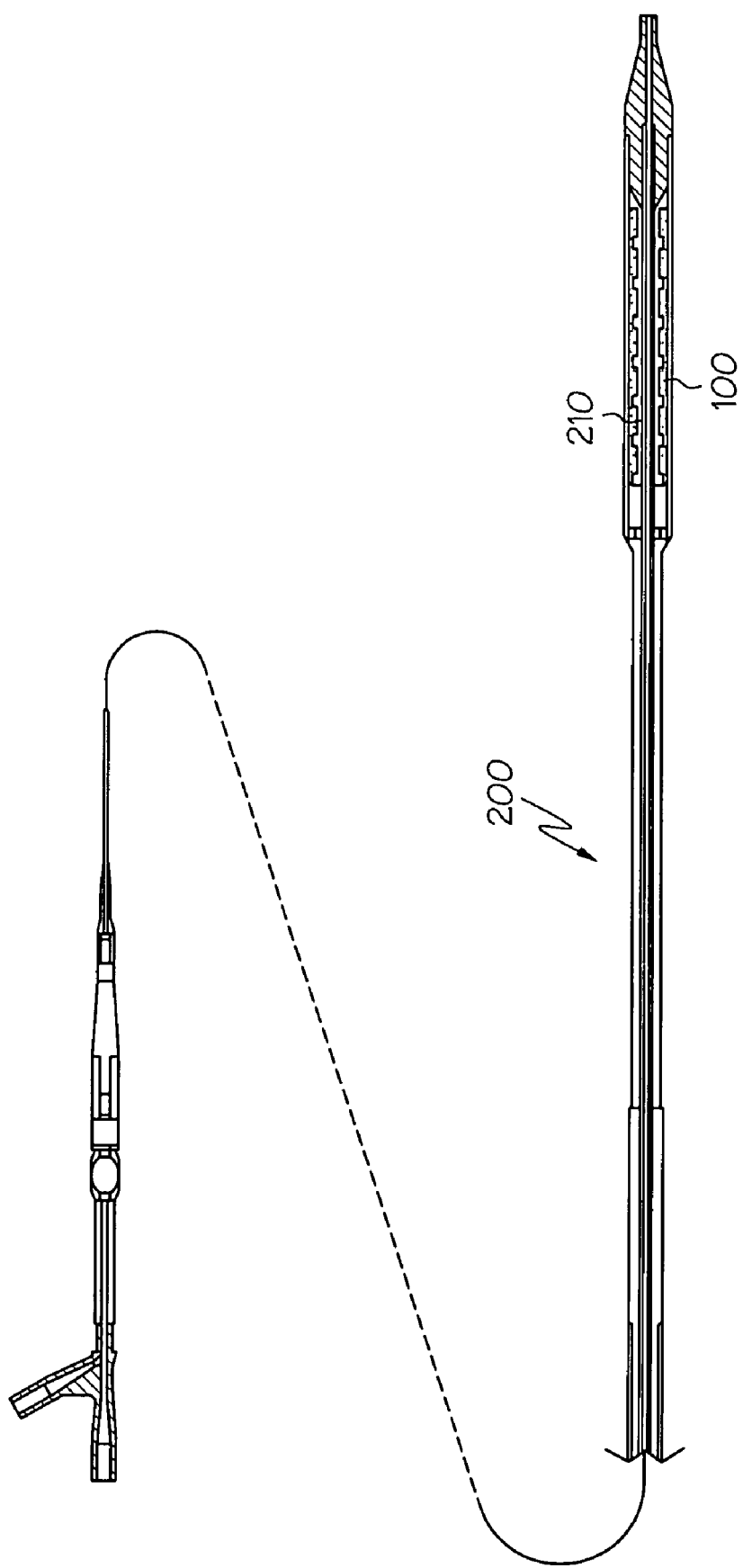
FIG. 3 shows a side view of a catheter taken in cross-section.

The invention is also directed to the combination of an inventive stent disclosed herein disposed on a catheter. Desirably, the stent is self-expanding and is restrained by a sheath. Suitable stent delivery devices such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in U.S. provisional application No. 60/238178. Desirably, where an inventive self-expanding stent is used, the stent has a restraining sheath disposed thereabout. An example of a catheter and stent is shown at 200 in FIG. 3. Catheter 200 includes a retractable sheath 210 which restrains self-expanding stent 100. Additional details concerning the catheter may be found in U.S. Pat. No. 5,957,930.

In practice the catheter may be inserted into a lumen, vessel or other body space in order to advance the portion of the catheter including the stent to a treatment site. It is known that such spaces, particularly vessels, may be rather confined and tortous in nature. As the distal end of the catheter is advanced through a body space, the stent mounted upon the catheter may be subjected to various inwardly acting and outwardly acting forces. For example, in the embodiment shown in FIG. 4, as the catheter 200 is advanced around a curved portion 222 of a vessel 220, inward facing portion 212 of the stent 100 will be subjected to a substantially longitudinally inward acting force as the stent is forced to bend around the curve 222. At the same time an outward facing portions 214 of the stent 100 is subjected to a substantially longitudinally outward acting force.

As is shown in the close-up view of FIG. 5, the substantially longitudinally inward acting force, indicated by arrows 216, causes, the peak portions 108b and 108c to flex in a manner which results in angle $\varnothing_1$ increasing.

As is shown in the close-up view of FIG. 6, however, the substantially longitudinally outwardly acting force, indicated by arrows 218, acting upon an individual outward facing portions 214 of the stent, will compress the peak portions 108b and 108c whereby angle $\varnothing_2$ is reduced.

The inventive stents may also be made from a single piece of material. For example, a sheet of super-elastic material may be provided and a stent pattern provided therein by laser cutting, etching, mechanical cutting or any other suitable method. Optionally, opposing edges of the sheet may be welded or otherwise joined to one another.

The inventive stents may likewise be made from a tube. The tube is provided with a stent design, as by laser cutting etching, mechanical cutting and the like.

The inventive stents may find use in the cerebral arteries as well as in the coronary arteries, the peripheral arteries and the arteries of the neck. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate. The inventive stents may be used interarterially in the brain, deployed across the neck of an aneurysm as well as in occlusions in bodily vessels. The size of the inventive stents will be appropriate for the intended usage of the stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent from claim 2; claim 5 may be taken as alternatively dependent on claim 2, or on claim 3; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent comprising a plurality of serpentine bands with a plurality of alternating peak portions and trough portions,
   the peak portions including at least two bent peak portions which bend toward one another, each of the bent peak portions wrapping at least partially about an adjacent peak,
   the trough portions including at least two bent troughs portions which bend toward one another, each of the bent trough portions wrapping at least partially about an adjacent trough,
   adjacent serpentine bands are connected one to the other via at least one connector extending from a peak portion of one serpentine band to a trough portion of an adjacent serpentine band.

2. The stent of claim 1 where adjacent serpentine bands are connected one to the other via a plurality of connectors extending from peak portions of one serpentine band to trough portions of an adjacent serpentine band.

3. The stent of claim 2 wherein the connectors are parallel to the longitudinal axis of the stent.

4. The stent of claim 2 wherein each connector has a first end and a second end, the first and second end circumferentially aligned one with the other.

5. The stent of claim 1 made of one or more shape memory materials.

6. The stent of claim 1 constructed and arranged to be self-expanding.

7. An unexpanded stent characterized by a longitudinal axis, the stent comprising a plurality of serpentine bands extending about the circumference of the stent,
   each serpentine band comprising a plurality of substantially straight struts,
      each strut having a first end and a second end,
      each two adjacent struts connected one to the other at a first end or a second but not both,
      adjacent struts which are connected at their first ends joined by a trough portion,
      adjacent struts which are connected at their second ends joined by a peak portion,
   each serpentine band including adjacent struts joined by a peak portion which together define an opening which extends parallel to the longitudinal axis of the stent,
   each serpentine band also including adjacent struts joined by a peak portion which together define an opening which includes a section which is parallel to the longitudinal axis of the stent and a section which is skewed relative to the longitudinal axis of the stent.

8. The stent of claim 1 comprising a plurality of the serpentine bands.

9. The stent of claim 8 wherein serpentine bands which are longitudinally adjacent one another are connected one to the other.

10. The stent of claim 8 wherein serpentine bands which are longitudinally adjacent one another are connected one to the other by at least one longitudinal connector extending from a shorter peak portion of one serpentine band to a shorter trough portion on a serpentine band which is longitudinally adjacent thereto.

11. The stent of claim 8 wherein serpentine bands which are longitudinally adjacent one another are connected one to the other by a plurality of longitudinal connectors which extend from shorter peak portions of one serpentine band to shorter trough portions on a serpentine band which is longitudinally adjacent thereto.

12. The stent of claim 11 wherein adjacent first and second bent trough portions which point away from one another are not separated by any shorter trough portions and adjacent first and second bent peak portions which point away from one another are not separated by any shorter peak portions.

13. The stent of claim 11 wherein adjacent first and second bent trough portions which point away from one another are not separated by any shorter trough portions, adjacent first and second bent peak portions which point away from one another are not separated by any shorter peak portions, adjacent first and second bent trough portions which point toward one another are separated one from the other by at least two shorter trough portions and adjacent first and second bent peak portions which point toward one another are separated one from the other by at least two shorter peak portions.

14. The stent of claim 1 made of one or more shape memory materials.

15. The stent of claim 1 constructed and arranged to be self-expanding.

16. In combination, a stent as in claim 15 disposed on a catheter, the stent restrained by a sheath.

17. The stent of claim 1 wherein the trough portions include at least two bent trough portions which bend toward one another, each of the bent trough portions wrapping at least partially about an adjacent trough.

18. The stent of claim 1 further comprising a coating, at least a portion of the stent having the coating thereon.

19. The stent of claim 18 wherein the coating is a matrix compound.

20. The stent of claim 18 wherein the coating is selected from at least one member of the group consisting of: lactide, glycolide, and caprolactone polymers and their copolymers; hydroxybutyrate and polyhydroxyvalerate and their block and random copolymers; a polyether ester; auhydrides, polymers and copolymers of sebacic acid, hexadecandioic acid; orthoesters; polydioxinone; polyglycolic acid and polylactic acid, their block and random copolymers and any combination thereof.

21. A stent characterized by a longitudinal axis, the stent comprising at least one serpentine band extending about the circumference of the stent and having alternating peak portions and trough portions, the peak portions including shorter peak portions and longer peak portions, the longer peak portions of a longitudinal extent greater than the shorter peak portions, the longer peak portions including first bent peak portions which extend in a first direction non-parallel to the longitudinal axis of the stent and second bent peak portions which extend in a second direction non-parallel to the longitudinal axis of the stent, each first bent peak portion circumferentially adjacent to one second bent peak portion which points toward the first bent peak portion and to one second bent peak portion which points away from the first bent peak portion, adjacent first and second bent peak portions which point toward one another separated one from the other by at least one shorter peak portion, the trough portions include shorter trough portions and longer trough portions, the longer trough portions of a longitudinal extent greater than the shorter trough portions, the longer trough portions including first bent trough portions which extend in a first direction non-parallel to the longitudinal axis of the stent and second bent trough portions which extend in a second direction non-parallel to the longitudinal axis of the stent, each first bent trough portion circumferentially adjacent to one second bent trough portion which points toward the first bent trough portion and to one second bent trough portion which points away from the first bent trough portion, adjacent first and second bent trough portions which point toward one another separated one from the other by at least one shorter trough portion.

* * * * *